(12) United States Patent
Zhu et al.

(10) Patent No.: US 9,387,469 B2
(45) Date of Patent: Jul. 12, 2016

(54) CARBONYLATION CATALYST AND PROCESS USING SAME

(71) Applicant: Eastman Chemical Company, Kingsport, TN (US)

(72) Inventors: Zhidong George Zhu, Kingsport, TN (US); Gerald Charles Tustin, Kingsport, TN (US); Joseph Robert Zoeller, Kingsport, TN (US); Craig Steven Dunn, Gray, TN (US); Larry Ronnie Lingerfelt, Blountville, TN (US); Mary Kathleen Moore, Jonesborough, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 14/143,349

(22) Filed: Dec. 30, 2013

(65) Prior Publication Data

US 2015/0182957 A1 Jul. 2, 2015

(51) Int. Cl.

| | |
|---|---|
| *C07C 67/36* | (2006.01) |
| *B01J 31/00* | (2006.01) |
| *B01J 31/26* | (2006.01) |
| *C07C 51/12* | (2006.01) |
| *B01J 21/08* | (2006.01) |
| *B01J 21/18* | (2006.01) |
| *B01J 29/08* | (2006.01) |
| *B01J 31/16* | (2006.01) |
| *B01J 31/18* | (2006.01) |

(52) U.S. Cl.
CPC *B01J 31/26* (2013.01); *B01J 21/08* (2013.01); *B01J 21/18* (2013.01); *B01J 29/084* (2013.01); *B01J 31/1616* (2013.01); *B01J 31/1633* (2013.01); *B01J 31/181* (2013.01); *B01J 31/1815* (2013.01); *C07C 51/12* (2013.01); *C07C 67/36* (2013.01); *B01J 2231/34* (2013.01); *B01J 2531/821* (2013.01); *B01J 2531/822* (2013.01); *B01J 2531/827* (2013.01); *B01J 2531/828* (2013.01)

(58) Field of Classification Search
CPC .......................... C07C 51/12; B01J 2531/822
USPC .................... 560/232; 562/519; 502/166, 330
See application file for complete search history.

(56) References Cited

U.S. PATENT DOCUMENTS

| | | |
|---|---|---|
| 3,308,069 A | 3/1967 | Wadlinger et al. |
| 3,702,886 A | 11/1972 | Argauer et al. |
| 3,832,449 A | 8/1974 | Rosinski |
| 3,972,983 A | 8/1976 | Ciric |
| 4,061,724 A | 12/1977 | Grose |
| 4,073,865 A | 2/1978 | Flanigen |
| 4,086,186 A | 4/1978 | Rubin et al. |
| 4,310,440 A | 1/1982 | Wilson et al. |
| 4,366,259 A | 12/1982 | Knifton |
| 4,440,871 A | 4/1984 | Lok et al. |
| 4,500,651 A | 2/1985 | Lok et al. |
| 4,554,143 A | 11/1985 | Messina et al. |
| 4,567,029 A | 1/1986 | Wilson |
| 5,155,261 A * | 10/1992 | Marston et al. ............... 562/519 |
| 5,576,458 A * | 11/1996 | Minami et al. ............... 562/519 |
| 6,916,951 B2 | 7/2005 | Tustin |
| 7,115,774 B2 | 10/2006 | Magna et al. |
| 7,368,597 B2 * | 5/2008 | Gaemers et al. ............... 562/519 |
| 2007/0191571 A1 | 8/2007 | Sink et al. |
| 2007/0191572 A1 | 8/2007 | Tustin et al. |
| 2007/0191573 A1 | 8/2007 | Sink et al. |
| 2007/0191575 A1 | 8/2007 | Sumner, Jr. et al. |
| 2007/0207917 A1 | 9/2007 | Sink et al. |

FOREIGN PATENT DOCUMENTS

| | | |
|---|---|---|
| CN | 102218343 A | 10/2011 |
| WO | 2006/122563 A1 | 11/2006 |
| WO | 2013/124174 A1 | 8/2013 |
| WO | 2013/124175 A1 | 8/2013 |

OTHER PUBLICATIONS

Gelin, P. et al.; "Corrdination Chemistry of Rhodium and Iridium in Constrained Zeolite Cavities: Methanol Carbonylation"; Pure & Appl. Chem., vol. 60, No. 8; pp. 1315-1320; 1988.
Howard, M. J. et al.; "$C_1$ to Acetyls: Catalysis and Process"; Catalysis Today, vol. 18, pp. 325-354; 1993.
Ishii, Hirotoshi et al.; "Oxidative carbonylation of phenol to Diphenyl carbonate catalyzed by Pd-pyridyl complexes tethered on polymer support"; Catalysis Communications, vol. 2, pp. 145-150; 2001.
Krzywicki, Andrzej and Marczewski, Marek; "Formation and Evolution of the Active Site for Methanol Carbonylation on Oxide Catalysts Containing $RhCl_3$"; Journal of Molecular Catalysis, vol. 6, pp. 431-440; 1979.
Maneck, H. E. et al.; "Heterogeneous Carbonylation of Methanol on Rhodium Introduced into Faujasite-Type Zeolites"; Catalysis Today, vol. 3, pp. 421-429; 1988.
Riisager, Anders et al.; "First application of supported ionic liquid phase (SILP) catalysis for continuous methanol carbonylation"; ChemComm www.rsc.org/chemcomm.com; received Nov. 17, 2005, accepted Dec. 15, 2005, published as an Advance Article Jan. 20, 2006; 3 pages.
Notification of Transmittal of the International Search Report and the Written Opinion of the International Searching Authority, or the Declarations date of mailing Apr. 3, 2015 received in corresponding International Application No. PCT/US2014/070761.

* cited by examiner

*Primary Examiner* — Sikarl Witherspoon
(74) *Attorney, Agent, or Firm* — James Arnold, Jr.

(57) ABSTRACT

Carbonylation catalysts and methods for using them are disclosed. In some embodiments, the carbonylation catalyst includes the contact product of:
(a) a nitrogen compound selected from monomeric pyridines and imidazoles;
(b) a Group VIII metal; and
(c) an alkali metal compound;
wherein the catalyst material is on a solid support.

10 Claims, No Drawings

CARBONYLATION CATALYST AND PROCESS USING SAME

FIELD OF THE INVENTION

The present invention relates to catalysts and processes for the carbonylation of alcohols.

BACKGROUND OF THE INVENTION

Carboxylic acids such as acetic acid have been known as industrial chemicals for many years. Acetic acid is used in the manufacture of a variety of intermediary and end-products. Many modern processes for producing such carboxylic acids are based on the carbonylation of alcohols such as methanol. Many acetic acid carbonylation processes have been developed and commercialized using homogeneous catalyst systems involving Group VIII metals such as rhodium, iridium, ruthenium and combinations of metals. Such homogeneous processes create the need to separate the catalyst from the product stream. Recovery of metals for reuse also becomes important because catalyst metals are often expensive. These issues create the need for additional construction and operating costs. Considerable effort has been directed to develop heterogeneous catalysis processes for carbonylation in which the catalyst material remains in a solid phase and thus remains separate from the product stream. One challenge of for such systems is ensuring stability of the catalyst metals and related compounds in the solid phase and resistance to leaching into the product. This is particularly true for liquid phase processes. Accordingly, there is a need for a catalyst which can be used in either a vapor phase or liquid phase carbonylation process for the production of carboxylic acids and their esters and in which the catalyst is maintained in the solid phase.

SUMMARY OF THE INVENTION

The invention thus provides carbonylation catalysts, processes that use carbonylation catalysts, and methods for making carbonylation catalyst. In some embodiments, the carbonylation catalyst includes the contact product of:
(a) a nitrogen compound selected from monomeric pyridines and imidazoles;
(b) a Group VIII metal; and
(c) an alkali metal compound;
wherein the catalyst material is on a solid support. In some embodiments, the Group VIII metal is selected from the group consisting of rhodium, ruthenium, cobalt, iridium, nickel, palladium, platinum and combinations thereof. In some embodiments, the Group VIII metal is rhodium. In some embodiments, the alkali metal compound is selected from lithium compounds.

In some embodiments, the monomeric nitrogen-containing compound is selected from compounds having the structure of Formulas I and II:

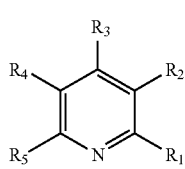

Formula I

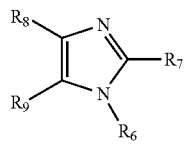

Formula II wherein $R_1$, $R_2$, $R_3$, $R_4$, $R_5$, $R_6$, $R_7$, $R_8$ and $R_9$ are independently selected from hydrogen, substituted or unsubstituted, linear or branched-chained $C_1$-$C_{20}$ alkyl, substituted or unsubstituted cyclic $C_3$-$C_{20}$ alkyl, and substituted or unsubstituted $C_6$-$C_{20}$ aryl. In some embodiments, the monomeric nitrogen-containing compound is a structure of Formula I, and $R_1$, $R_2$, $R_4$, and $R_5$ are each independently selected from hydrogen and $C_1$-$C_3$ alkyl and $R_3$ is a phenyl group, tje phenyl group being optionally substituted with a $C_1$-$C_{12}$ alkyl in a para-configuration around the phenyl ring with the other six-membered ring shown in Formula I. In some embodiments, $R_1$, $R_2$, $R_4$, and $R_5$ are each hydrogen. In some embodiments, the $R_3$ is a phenyl group that is optionally substituted with a $C_1$-$C_3$ alkyl in a para-configuration around the phenyl ring with the other six-membered ring shown in Formula I. In some embodiments, nitrogen-containing monomeric nitrogen-containing compound is 4-phenyl-pyridine.

In some embodiments, the monomeric nitrogen-containing compound is a structure of Formula II, and $R_7$, $R_8$, and $R_9$ are each independently selected from hydrogen and $C_1$-$C_3$ alkyl and $R_6$ is a phenyl group, said phenyl group being optionally substituted with a $C_1$-$C_{12}$ alkyl in a para-configuration around the phenyl ring with the five-membered ring shown in Formula II. In some embodiments, $R_7$, $R_8$, and $R_9$ are each hydrogen. In some embodiments, wherein $R_6$ is a phenyl group that is optionally substituted with a $C_1$-$C_3$ alkyl in a para-configuration around the phenyl ring with the five-membered ring shown in Formula II.

In some embodiments, solid support is selected from the group consisting of silicas, polymers, zeolites, molecular sieves, clays, alumina, titania, zirconia, carbon, activated carbon and mixtures thereof. In some embodiments, solid support possesses at least some pores having a minimum diameter between about 5 and about 10 Angstroms. In some embodiments, the carbonylation catalyst of claim 24 solid support is selected from Y zeolites.

In some embodiments, catalyst includes from about 0.1 weight percent to about 2 weight percent each of said Group VIII metal and said at least one alkali metal, wherein the weight % is based on the weight % of the metal.

The invention further provides Carbonylation process for the production of esters, carboxylic acids or combinations of two or more of the foregoing, which includes combining in a reaction zone at least one carbonylation feedstock compound selected from alkanols, dialkyl ethers, and combination of any two or more thereof with carbon monoxide in a carbonylation zone of a carbonylation reactor in the presence of a catalyst material, wherein the catalyst material is any of the catalysts described above. In some embodiments, the carbonylation feedstock compound is methanol. In some embodiments, the carbonylation process occurs in the liquid phase. In some embodiments, the carbonylation process occurs in the vapor phase. In some embodiments, the process further includes contacting said carbonylation feedstock compound in said carbonylation zone with a promoter compound selected from iodine, bromine, chlorine, hydrogen halides, gaseous hydriodic acid, alkyl and aryl halides having up to 12 carbon atoms, and combinations of two or more of the foregoing. In some embodiments, the promoter compound is selected from hydrogen iodide, methyl iodide, ethyl iodide, 1-iodopropane, 2-iodobutane, 1-iodobutane, hydrogen bromide, methyl bromide, ethyl bromide, benzyl iodide and mixtures thereof. In some embodiments, the promoter compound is selected from the group consisting of hydrogen iodide, methyl iodide, hydrogen bromide, methyl bromide and mixtures thereof.

DETAILED DESCRIPTION OF THE INVENTION

The invention provides catalysts useful for the production of carboxylic acids and esters by reacting alcohols, ethers and ester-alcohol mixtures in a carbonylation process. The catalyst has been found to operate in both liquid or vapor-phase carbonylation processes. The catalyst includes an effective amount of a Group VIII metal, at least one alkali metal compound and a monomeric nitrogen-containing compound associated with a solid support. The invention further provides carbonylation processes using such catalysts.

Catalyst

The catalysts of the present invention contain the contact product of a nitrogen compound, a Group VIII metal and an alkali metal compound. These components are supported on a solid support.

The Group VIII metal of the catalyst may be any Group VIII metal which will catalyze the carbonylation of reactant compounds with carbon monoxide. In some embodiments, the Group VIII metals are selected from rhodium, ruthenium, cobalt, iridium, nickel, palladium, platinum or a combination of two or more of the foregoing. In some embodiments the Group VIII metal is rhodium, iridium, nickel, cobalt, and palladium or a combination of two or more of the foregoing. In some embodiments, the Group VIII metal is rhodium. The form of the Group VIII metal is not critical and any form of metal or metallic compound. Some examples of Group VIII metal compounds which include those containing a halide, trivalent nitrogen, organic compounds of trivalent nitrogen, carbon monoxide, hydrogen, carboxylate and 2,4-pentanedione, either alone or in combination. Some examples of suitable Group VIII species include rhodium trichloride hydrate, iridium trichloride hydrate, nickel iodide hydrate, palladium acetate and palladium chloride. These compounds are generally commercially available. In some embodiments, the Group VIII metal species is at least partially soluble in water or an organic solvent and in some embodiments will react with compounds containing nitrogen to form a metal complex. In some embodiments, the Group VIII metal is selected from rhodium, iridium and mixtures thereof.

The alkali metal compound includes any alkali metal in any useful compound or form. In some embodiments, the alkali metal is selected from lithium, sodium, potassium and combinations of two or more of the foregoing. In some embodiments, the alkali metal is lithium. Some examples of compounds in which the alkali metal may be present include halides, acetates, nitrates, carbonates and hydroxides, either alone or in combinations of two or more of the foregoing. In some embodiments, the alkali metal compound is soluble in water. In some embodiments, the alkali metal compound is selected from acetates, nitrates, halides and combinations thereof.

The weight percentage of the Group VIII and alkali metal in the catalyst may vary considerably depending on the identities of the Group VIII metals. Each of the metals, based on the weight of the metal, may range from about 0.01 to about 10 weight % of the catalyst total weight. In some embodiments, each of the metal weight percentages range from about 0.1 to about 2 weight %, based on the weight of the metal.

The monomeric nitrogen-containing compound is selected from pyridines, imidazoles and combinations thereof. By "monomeric" it is meant that the compound does not include more than one pyridine or imidazole group. In some embodiments, the monomeric nitrogen-containing compound is selected from compounds having the structure of Formulas I and II:

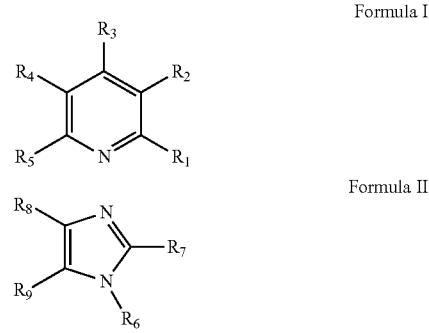

Formula I

Formula II wherein $R_1$, $R_2$, $R_3$, $R_4$, $R_5$, $R_6$, $R_7$, $R_8$ and $R_9$ are independently selected from hydrogen, substituted or unsubstituted, linear or branched-chained $C_1$-$C_{20}$ alkyl, substituted or unsubstituted cyclic $C_3$-$C_{20}$ alkyl, and substituted or unsubstituted $C_6$-$C_{20}$ aryl. Some examples of alkyl moieties of the substituents mentioned above include methyl, ethyl, n-propyl, iso-propyl, cyclo-propyl, n-butyl, iso-butyl, sec-butyl, tert-butyl, n-pentyl, n-hexyl, cyclo-hexyl, n-octyl, and iso-octyl. Some examples of aryl groups include phenyl, benzyl, and ethyl-phenyl. As examples of substituents of the above alkyl and aryl groups may be mentioned, without limitation, include halogen, such as fluoro, chloro, bromo or iodo, hydroxy, $C_1$-$C_6$ alkyl, and $C_1$-$C_6$ alkoxy. In some embodiments, the monomeric nitrogen-containing compound is a structure of Formula I. In some embodiments, the monomeric nitrogen-containing compound is a structure of Formula II.

In some embodiments in which the monomeric nitrogen-containing compound is a structure of Formula I, $R_3$ is a phenyl group and $R_1$, $R_2$, $R_4$, and $R_5$ are each independently selected from hydrogen and $C_1$-$C_3$ alkyl. In some embodiments in which the monomeric nitrogen-containing compound is a structure of Formula I, $R_3$ is a phenyl group and $R_1$, $R_2$, $R_4$, and $R_5$ are each hydrogen. In some embodiments, the phenyl group referenced in this paragraph is substituted with is substituted with a $C_1$-$C_{12}$ alkyl in a para-configuration around the phenyl ring with the other six-membered ring shown in Formula I. In some embodiments, the in some embodiments the alkyl referred to in the previous sentence is a $C_1$-$C_3$ alkyl.

In some embodiments in which the monomeric nitrogen-containing compound is a structure of Formula II, $R_6$ is a phenyl group and $R_7$, $R_8$, and $R_9$ are each independently selected from hydrogen and $C_1$-$C_3$ alkyl. In some embodiments in which the monomeric nitrogen-containing compound is a structure of Formula II, $R_6$ is a phenyl group and $R_7$, $R_8$, and $R_9$ are each hydrogen. In some embodiments, the phenyl group referenced in this paragraph is substituted with a $C_1$-$C_{12}$ alkyl in a para-configuration around the phenyl ring with the five membered ring shown in Formula II. In some embodiments, the in some embodiments the alkyl referred to in the previous sentence is a $C_1$-$C_3$ alkyl.

In some embodiments, the monomeric nitrogen-containing compound is selected from 3-methylimidazole, 3,4-dimethylimidazole, 2,3,4,5-tetramethylimidazole, n-phenyl imidazole, pyridine, 2-phenyl-pyridine, 3-phenyl-pyridine, 4-phenyl-pyridine, 4-(4'-methyl phenyl)-pyridine and mixtures thereof. In some embodiments, the monomeric nitrogen-containing compound or their quaternary salts that result from reaction with methyl iodide have a boiling point of about 180° C. or greater.

In some embodiments, the molar ratio of monomeric nitrogen-containing compound to Group VIII metal may be from about 0.1 to about 100. In some embodiments, the molar ratio is from about 0.5 to about 10, or from about 1 to about 10.

Any suitable support material may be used. In some embodiments, the support materials are selected from the group consisting of silicas, polymers, zeolites, molecular sieves, clays, alumina, titania, zirconia, carbon, activated carbon and combinations thereof. In some embodiments, the support material is selected from zeolites and carbons (including activated carbons). In some embodiments, the support material is selected from zeolites.

In some embodiments, the support material is a porous material possessing at least some pores having a minimum diameter of from about 3 to about 12 Angstroms (Å). In some embodiments, the support material possesses at least some pores having a minimum diameter of from about 5 to about 10 Angstroms. In some embodiments, the support material possesses at least some pores having a minimum diameter of from about 6 to about 9 Angstroms.

Some examples of zeolites useful in this invention include, for example, LZ-10, LZ-20, 4A, 5A, 13X, 10X, Y, SK40, SK41, chabazite, faujasite, levynite, gismondine, erionite, sodalite, analcime, gmelinite, harmotome, mordenite, epistilbite, heulandite, stilbite, edingtonite, mesolite, natrolite, scolecite, thomsonite, brewsterite, laumontite, phillipsite, the ZSM's (ZSM-5, ZSM-20, ZSM-12, and ZSM-34), and the like, including mixtures thereof. Other examples are disclosed in U.S. Pat. Nos. 3,702,886, 3,972,983, 3,832,449, 4,086,186 and 3,308,069, and R. Szostak, *Handbook of Molecular Sieves*, Kluwer Academic Publishers, Dordrecht, Netherlands (1992). Some examples of molecular sieves useful in this invention include, for example, the silica molecular sieves, such as silicalite. Some examples of silica molecular sieves are described in U.S. Pat. Nos. 4,061,724 and 4,073,865. Other molecular sieves useful in this invention include crystalline microporous molecular sieve oxides that are based on the presence of aluminophosphate in the framework of the crystal structures, e.g., those commonly known by the acronyms SAPO, MeAPO, FAPO, MAPO, MNAPO, CoAPO, ZAPO, MeAPSO, FAPSO, MAPSO, MnAPSO, CoAPSO, ZAPSO, EIAPO, EIAPSO and the like, including mixtures thereof. Such molecular sieves are described, for example, in U.S. Pat. Nos. 4,567,029, 4,440,871, 4,500,651, 4,554,143 and 4,310,440. In some embodiments, the support material is a Y zeolite.

Mesoporous materials with pore sizes of about 20-500 Angstroms can also be used as the support. Some examples of these materials include MCM-41, MCM-48, SBA-15, SBA-16, FDU-5, FDU-12, KIT-5, KIT-6 and the like. These materials may be synthesized, for example using cetyltrimethylammonium bromide(CTAB), commercially available poly(ethylene oxide)-b-poly(propylene oxide)-b-poly(ethylene oxide) (PEO-PPO-PEO) triblock copolymers, high molecular weight poly(isoprene)-b-poly(ethylene oxide) (PI-PEO) block copolymers, or high-molecular-weight polystyrene-b-poly(ethylene oxide) copolymer (PS215-PEO100) as a template. In some embodiments, the as-synthesized material is calcined under nitrogen/air to remove the template.

Any suitable forms of carbon can be used as supports for this invention. In some embodiments, the carbon support material is selected from activated carbon, carbon black and graphite or graphitised materials. Activated carbon can be manufactured from suitable precursors in at least two ways: chemical activation and physical activation. In some embodiments, chemically activated carbons are manufactured by the simultaneous carbonization and activation of the raw material at from about 600 to about 800° C. The activating agent for this process, e.g. $H_3PO_4$ or $ZnCl_2$, can be incorporated into the raw material before heating starts. Physically or so-called steam activated carbons can be manufactured, for example, from a pre-carbonized material which is obtained by thermal decomposition of a carbonaceous precursor at from about 600 to about 800° C. in the absence or under controlled admission of air. The activation step is usually performed in the presence of steam and/or $CO_2$ at from about 800 to about 1100° C.

Spherical activated carbons produced from resol type phenolic resin beads that do not contain a pore forming agent are also suitable as a support for the present catalyst. In some embodiments, the resin is produced using ammonia or an amine catalyst so that the final resin consists essentially of carbon, hydrogen, oxygen and small amounts of nitrogen. The methods provided in US patent applications 2007/0207917 A1, 2007/01191575 A1, 2007/0191573 A1, 2007/0191572 A1 and 2007/0191571 A1, are suitable for making the starting resol type spherical resin beads. These beads can be activated to form carbon beads which useful as support of carbonylation catalyst of this invention.

In some embodiments, support materials have a size of from about 400 mesh per inch to about ½ inch. In some embodiments, the support is carbon, including activated carbon, having a high surface area. In some embodiments, the carbon has a surface area of from about 200 square meters/gram ($m^2/g$) to about 1200 $m^2/g$. The shape of the solid support is not particularly important and can be regular or irregular and include extrudates, rods, balls, broken pieces and the like disposed within the reactor.

In some embodiments, the present supported catalyst includes a catalytically active metal selected from Rhodium, a lithium compound and a monomeric nitrogen-containing compound confined on a porous zeolite or carbon support. Embodiments of the catalyst are stable for both vapor and liquid phase methanol carbonylation. Although not to be bound by any theory, it is believed that the combination of alkali metal and monomeric nitrogen-containing compound on the support accelerates the carbonylation rate and stabilizes the active species in the support.

The amount of Group VIII and alkali metal on the support can vary from about 0.01 weight percent to about 10 weight percent, based on the weight of the metal. In some embodiments, the amount of Group VIII and alkali metal on the support can vary from about 0.1 weight percent to about 5 weight percent, based on the weight of the metal. In some embodiments, the amount of Group VIII and alkali metal on the support can vary from about 0.1 weight percent to about 2 weight percent, based on the weight of the metal.

Preparing the solid support catalyst may be carried out by any effective means. In some embodiments, it is provided by providing a solid support described above; contacting support material with a solution containing the Group VIII metal and drying the support material; contacting the Group VIII metal source with one or more monomeric nitrogen-containing compound in an organic solvent followed by impregnating the metal complex into the support. In some embodiments, the Group VIII metal can be impregnated into the support first and then forming a metal complex in the support matrix by reacting the Group VIII metal source with one or more of the monomeric nitrogen-containing compounds. The liquid used to deliver the active metal in the form a solution, dispersion, or suspension typically is a liquid having a low boiling point, i.e., high vapor pressure at a temperature of from about 10° C. to about 140° C. Examples of suitable solvents include carbon tetrachloride, benzene, acetone, methanol, ethanol, isopropanol, isobutanol, pentane, hexane, cyclohexane, heptane, toluene, acetaldehyde, acetic acid, water, and tetrahydrofuran. The solid support is then contacted and desirably impregnated with the alkali metal or a metal complex containing solution. Various methods of contacting the support material with the Group VIII may be employed. The solvent or liquid is evaporated, i.e. the solid support is dried so that at least a portion of the Group VIII is associated with the solid support. In some embodiments, drying temperatures can range from about 100° C. to about 600° C. The alkali metal can be impregnated into the support in a similar way.

Carbonylation Process

The invention also provides carbonylation processes for the production of esters, carboxylic acids or combinations of two or more of the foregoing in which one or more carbonylation feedstock compounds is combined with carbon monoxide in a carbonylation zone of a carbonylation reactor in the presence of the catalyst of the present invention. Some examples of feedstock compounds include from alkanols, dialkyl ethers, i.e., compounds in which an aliphatic carbon atom is directly bonded to an oxygen atom of either an alcoholic hydroxyl group in the compound or an ether oxygen in the compound and may further include aromatic moieties. In some embodiments, the feedstock compound is selected from alkyl alcohols having from 1 to 10 carbon atoms, alkane polyols having 2 to 6 carbon atoms, alkyl alkylene polyethers having 3 to 20 carbon atoms and alkoxyalkanols having from 3 to 10 carbon atoms and combinations of two or more of the foregoing. In some embodiments, the feedstock compound is selected from one or more alkyl alcohols having from 1 to 6 carbon atoms and combinations thereof. In some embodiments, the feedstock compound is methanol. In some embodiments, methanol is supplied in the form of a combination of materials that generate methanol. Some examples of such combinations include (i) methyl acetate and water and (ii) dimethyl ether and water. In some embodiments, methyl acetate and dimethyl ether are can form within the reactor and, if methyl acetate is not the desired product, it can optionally be recycled with water to the reactor for conversion is converted to acetic acid.

While water in the gaseous or liquid feed mixture is not essential when using a methanol feed, the presence of some water is may be used in some embodiments to suppress accumulation of methyl acetate and/or dimethyl ether which are formed by esterification of acetic acid and methanol dehydration respectively. When using methanol to generate acetic acid, the molar ratio of water to methanol in some embodiments can be from about 0:1 to about 10:1, and in some embodiments from about 0.01:1 to about 1:1. When using an alternative source of methanol such as methyl acetate or dimethyl ether, the amount of water fed usually may optionally be increased to account for the mole of water required for hydrolysis of the methanol alternative. Accordingly, when using either methyl acetate or dimethyl ether, the mole ratio of water to ester or ether in some embodiments is from about 1:1 to about 10:1, and in some embodiments from about 1:1 to about 3:1.

In some embodiments in which the vapor-phase or liquid carbonylation process is used to produce methyl acetate, dimethyl ether is used as a feedstock and water is not added (except to the extent already present in other feeds The carbon monoxide utilized in the process can be a purified carbon monoxide or can include other gases. The purity of the carbon monoxide feed is not limiting and in some embodiments can be from about 33% by volume to about 100% by volume carbon monoxide, and in some embodiments is from about 70% by volume to about 99.99% by volume carbon monoxide. The remainder of the gas mixture may include any gases that do not undesirably interfere with the process. Some examples include nitrogen, hydrogen, carbon dioxide, water and paraffinic hydrocarbons having from one to four carbon atoms. In some embodiments, hydrogen is present and the ratio of carbon monoxide to hydrogen ranges from about 99:1 to about 2:1, and in some embodiments the range is from about 95:5 to about 99.9:1 CO to hydrogen.

In some embodiments, a halogen compound is included and aids in the carbonylation process. In some embodiments, the halogen compound is selected from bromine and iodine compounds. Some examples of halogen compound that may be sued include hydrogen compounds such as hydrogen iodide and gaseous hydroiodic acid; alkyl and aryl halides having up to about 12 carbon atoms such as methyl iodide, ethyl iodide, 1-iodopropane, 2-iodobutane, 1-iodobutane, methyl bromide, ethyl bromide, benzyl iodide and combinations of any two or more of the foregoing. In some embodiments, the halogen compound is a hydrogen halide or an alkyl halide having up to about 6 carbon atoms. In some embodiments, the halogen compound is selected from hydrogen iodide, methyl iodide, hydrogen bromide, methyl bromide and combinations of two or more of the foregoing. The halogen compound may also be a molecular halogen such as $I_2$, $Br_2$ or $Cl_2$. In some embodiments, the halogen compound is iodide. In some embodiments, the halogen compound is selected from methyl iodide, hydrogen iodide and molecular iodine. In some embodiments, the halogen compound is methyl iodide.

The amount of halogen compound can be useful in any useful amount. In some embodiments, the halogen compound is present in a molar ratio of from about 1:1 to about 10,000:1 of total carbonylation feedstock compounds to halogen compounds. In some embodiments, the ration is from about 5:1 to about 1000:1.

One or more carbonylation feedstock compounds (along with carbon monoxide and any other feeds) are contacted the catalyst of the invention. In some vapor-phase embodiments, this can accomplished by passing the vapor feeds across the catalyst. The process can be operated at any useful pressure and temperature. In some embodiments of liquid phase operations, pressure is from 1 to 500 bar. In some liquid-phase embodiments, pressure is from about 1 to about 150 bar absolute. In some liquid-phase embodiments, the pressure is from about 40 to about 80 bar absolute. In some liquid-phase embodiments, the pressure is from about 50 to about 70 bar absolute. In some liquid phase embodiments, the operating temperature is from about 50° C. to about 500° C. In some liquid phase embodiments, the operating temperature is from about 100° C. to about 300° C. In some liquid phase embodiments, the operating temperatures are from about 150° C. to about 200° C. In some liquid phase embodiments, the operating temperature is from 150° C. to 250° C.

In some embodiments, vapor-phase carbonylation is operated at temperatures above the dew point of the product mixture, i.e., the temperature at which condensation occurs. However, since the dew point is a complex function of dilution (particularly with respect to non-condensable gases such as unreacted carbon monoxide, hydrogen, or inert diluent gas), product composition, and pressure, this may still be operated over a wide range of temperatures. In some vapor-phase embodiments, the temperature is from about 100° C. to about 500° C., and vapor-phase embodiments also exist in which temperature is from about 100° C. to about 325° C. or from about 150° C. to about 275° C. In some vapor-phase embodiments pressures are from about 1 to about 100 bar absolute. Vapor-phase embodiments also exist in which the pressure is from about 1 to about 50 bars absolute or from about 3 to about 30 bar absolute.

The present invention is illustrated in greater detail by the specific examples present below. It is to be understood that these examples are illustrative embodiments and are not intended to be limiting of the invention, but rather are to be construed broadly within the scope and content of the appended claims.

In the examples which follow all of the catalysts were prepared in a similar manner except as specified otherwise.

Example 1

Example 1 illustrates the preparation and use of rhodium, pyridine and lithium on Y zeolite (Rh-Py/Li/Y zeolite) as the supported catalyst for the vapor phase carbonylation of methanol to acetic acid (HOAc) and methyl acetate (MeOAc) in a fixed bed.

Rh-Py/Li/Y zeolite was synthesized according to the following procedure. 0.5719 g of $RhCl_3 \cdot x\ H_2O$ (40% Rh) was dissolved in 20 g of deionized water and then using a rotary evaporator, impregnated into 20 g of 20-40 mesh crushed Y zeolite (available from Strem Chemicals, Newburyport, Mass. 01950) having a silica/alumina ratio of 5.6. The mixture was heated using a water bath at a temperature of 60° C. and evacuated under 30 Torr until the support was dry. The material was then transferred to a quartz tube containing a quartz wool support plug. The quartz tube was placed into the Lindberg electric furnace and heated in an upward flow of nitrogen (100 standard cubic centimeters per minute (SCCM)) over a 2 hour period to 300° C. and held at 300° C. for 2 hours before cooling back to ambient temperature. The Rh/Y recovered from the quartz tube was then refluxed with a solution 5 ml pyridine in 25 ml of $CH_2Cl_2$ for 2 hours and then dried under vacuum. The resulting Rh-Py/Y was then impregnated with a solution prepared from dissolving 1.323 g LiI in 20 ml deionized water. The mixture again was dried under vacuum and then transferred to a quartz tube containing a quartz wool support plug. The quartz tube was placed into the Lindberg electric furnace and heated in an upward flow of nitrogen (100 SCCM) over a 2 hour period to 300° C. and held at 300° C. for 2 hours before cooling back to ambient temperature to obtain the final catalyst suitable for the methanol carbonylation reaction.

The vapor phase reactor was constructed entirely of Hastelloy C alloy. Reactants entered the base of the reactor via a 0.375 inch (9.5 mm) outer diameter (O.D.) inlet tube having a wall thickness of 0.065 inch (1.65 mm). The portion above the inlet tube expanded as a collar piece as a cone into a cylindrical section having a 0.625-inch (1.6 cm) inner diameter (I.D.) and a wall thickness of 0.1875 inch (4.8 mm) with overall length of 2.00 inches (5.1 cm). The top 0.38-inch (9.7 mm) portion of the collar was machined to a diameter of 0.750 inch (1.9 cm). The machined portion of the collar contained a 0.735-inch (1.87 cm) diameter by 0.0625-inch (1.65 mm) thick Hastelloy C alloy 5 micron metal filter, which acted as a gas dispersion device and support for the catalyst. The filter and the collar containing the filter were welded to a 6.25-inch (15.9 cm) long by 0.625-inch (1.6 cm) I.D./0.750-inch (1.9 cm) O.D. Hastelloy C alloy reaction tube. The reaction tube was welded to an expanded zone increasing in a conical fashion at 45 degrees to an outer diameter of 1.50 inches (3.81 cm), continuing in a cylindrical fashion for another 1.83 inches (4.65 cm) and then decreasing at a 45-degree angle and welded to a 4.50 inch (11.4 cm) long by 0.375-inch (9.5 mm) O.D. loading and sensing tube. The vertical loading and sensing tube contained a 0.375-inch (9.5 mm) O.D. pressure transducer side arm located 2.0 inches (5.1 cm) above the expanded zone and positioned at 45 degrees from vertical of the loading and sensing tube. Vapor product was removed from the expanded zone through a 0.250 inch (6.36 mm) O.D. product removal line connected approximately half the vertical distance of the expanded zone. The product removal line exited the reactor horizontally and then bent downward.

Metered gas flows were maintained by Brooks 5850 Series E mass flow controllers interfaced with a Camile™ 3300 Process Monitoring and Control System. Temperature control was also provided by the Camile™ 3300 Process Monitoring and Control System. Liquid feed was provided by an Alltech 301 HPLC pump. Liquid and gas feeds were vaporized by feeding to a heated Hastelloy C alloy vaporizer maintained at 150° C. and transported in the vapor phase through a transfer line at 150° C. to the base of the reactor inlet tube. Heat to the reactor was provided by three separate split aluminum blocks with each split aluminum block surrounded by band heaters. Each split aluminum block heating unit had its own temperature control provided by the Camile™ 3300 Process Monitoring and Control System. The bottom heater provided heat to the reactor inlet tube and collar piece. The central heater provided heat to the reaction tube section. The top heater provided heat to the expansion zone.

The end of the product removal line was connected to a 50 micron filter attached to a Hastelloy C alloy condenser, which was attached to a Hastelloy C alloy product collection tank with a working capacity of one liter. The pressure was maintained using a Tescom Model 44-2300 backpressure regulator attached to a vent line on the top of product collection tank. Liquid samples were collected from a valve at the base of the liquid collection tank. The carbonylation products were weighed and analyzed by gas chromatography using a Hewlett Packard Model 6890 gas chromatograph fitted with a 30 m×0.25 mm DB_FFAP capillary column (0.25 micron film thickness) programmed at 40° C. for 5 minutes, 25° C./minute to 240° C. and holding at 240° C. for 1 minute using a thermal conductivity detector held at 250° C. (injector temperature=250° C.). Mixtures were prepared for gas chromatographic analysis by adding 5 ml tetrahydrofuran solution containing 2 wt % decane internal standard to an accurately weighed sample of the product mixture.

The reactor was loaded with 6.4922 g (10 mL) of the Rh-Py/Li/Y zeolite made above through the top of the reactor. The reactor was then pressurized to 200 psig with carbon monoxide (150 SCCM). Then the vaporizer was set for 150° C. and the three reactor heaters were set for 190° C. with CO flowing at 150 SCCM through the base of the reactor. After the reactor temperature had stabilized at 190° C. at 200 psig, a solution containing methanol and methyl iodide in a weight ratio of 70 methanol/30 methyl iodide was fed to the reactor system at 0.107 ml/minute while maintaining the carbon monoxide flow at 150 SCCM. The results are reported in Table I below.

TABLE I

| Hours | % MeOH conversion | moles MeOAc/L-hr | moles HOAc/L-hr | Net moles acetyl/L-hr |
|---|---|---|---|---|
| 2 | 99.62 | 0.28 | 2.59 | 2.87 |
| 4 | 98.41 | 1.69 | 9.38 | 11.07 |
| 6 | 98.44 | 1.87 | 8.54 | 10.41 |
| 21 | 98.44 | 2.31 | 8.04 | 10.34 |
| 23 | 98.40 | 2.32 | 7.40 | 9.73 |
| 25 | 98.39 | 2.51 | 7.37 | 9.88 |
| 27 | 98.38 | 2.35 | 7.29 | 9.64 |
| 29 | 98.48 | 2.30 | 7.17 | 9.48 |
| 31 | 98.44 | 2.37 | 6.99 | 9.36 |
| 45 | 98.33 | 2.58 | 7.28 | 9.86 |
| 47 | 98.23 | 2.52 | 6.82 | 9.34 |
| 49 | 98.28 | 2.46 | 6.90 | 9.36 |
| 51 | 98.41 | 2.48 | 6.74 | 9.22 |
| 53 | 98.33 | 2.61 | 7.12 | 9.73 |
| 55 | 98.39 | 2.51 | 6.83 | 9.33 |
| 69 | 98.32 | 2.61 | 7.12 | 9.73 |
| 73 | 98.26 | 2.67 | 6.50 | 9.18 |
| 77 | 98.16 | 2.68 | 6.40 | 9.08 |
| 93 | 98.10 | 2.79 | 6.35 | 9.14 |
| 96 | 98.02 | 2.89 | 5.89 | 8.78 |
| 121 | 97.31 | 3.19 | 5.28 | 8.47 |
| 145 | 95.44 | 3.48 | 3.80 | 7.27 |
| 165 | 90.97 | 3.80 | 2.38 | 6.18 |
| 189 | 84.74 | 3.67 | 1.44 | 5.11 |
| 213 | 77.05 | 3.40 | 0.78 | 4.18 |
| 237 | 66.62 | 2.69 | 0.37 | 3.06 |
| 261 | 59.29 | 2.15 | 0.17 | 2.33 |

Example 2

Example 2 illustrates the preparation and use of rhodium, 4-phenylpyridine and lithium on Y zeolite (Rh-PhPy/Li/Y) for the vapor phase carbonylation of methanol to acetic acid (HOAc) and methyl acetate (MeOAc) in a fixed bed Rh-PhPy/Li/Y zeolite was synthesized according to the following procedure. 0.5239 g of RhCl$_3$.x H2O (40% Rh) was dissolved in 20 g of deionized water and then using a rotary evaporator impregnated into 20 g of 20-40 mesh crushed Y zeolite (available from Zeolyst International, Conshohocken Pa., 19428) having a silica/alumina ratio of 80. The mixture was heated under water bath temperature 60° C. and evacuated under 30 Torr until it became dry. The material was then transferred to a quartz tube containing a quartz wool support plug. The quartz tube was placed into the Lindberg electric furnace and heated in an upward flow of nitrogen (100 SCCM) over a 2 hour period to 300° C. and held at 300° C. for 2 hours before cooling back to ambient temperature. The Rh/Y recovered from the quartz tube was then refluxed with a solution with 9.5924 g of 4-phenylpyridine in 25 ml of CH$_2$Cl$_2$ for 2 hours, and then dried under vacuum. The resulting Rh-PhPy/Y was then impregnated with a solution prepared from dissolving 1.3264 g LiI in 20 ml deionized water. The mixture again was dried under vacuum and then transferred to a quartz tube containing a quartz wool support plug. The quartz tube was placed into the Lindberg electric furnace and heated in an upward flow of nitrogen (100 SCCM) over a 2 hour period to 300° C. and held at 300° C. for 2 hours before cooling back to ambient temperature to obtain the final catalyst suitable for the methanol carbonylation reaction.

The reactor was loaded with 5.4972 g (10 mL) of the Rh-PhPy/Li/Y zeolite made above through the top of the reactor. The methanol carbonylation condition was the same as Example 1. The results are reported in Table II below.

TABLE II

| Hours | % MeOH conversion | moles MeOAc/L-hr | moles HOAc/L-hr | Net moles acetyl/L-hr |
|---|---|---|---|---|
| 2 | 95.41 | 1.06 | 3.33 | 4.38 |
| 5 | 97.39 | 1.71 | 7.47 | 9.19 |
| 24 | 98.30 | 2.27 | 8.84 | 11.10 |
| 48 | 98.25 | 2.55 | 8.44 | 10.99 |
| 72 | 98.25 | 2.55 | 8.41 | 10.96 |
| 96 | 98.20 | 2.59 | 8.22 | 10.81 |
| 120 | 96.77 | 3.79 | 5.37 | 9.17 |
| 144 | 96.33 | 3.84 | 5.18 | 9.02 |
| 168 | 97.01 | 3.53 | 5.77 | 9.30 |
| 192 | 96.97 | 3.59 | 5.43 | 9.01 |
| 216 | 96.76 | 3.68 | 5.18 | 8.86 |
| 240 | 96.65 | 3.71 | 5.16 | 8.87 |
| 264 | 96.57 | 3.80 | 4.93 | 8.74 |
| 288 | 96.42 | 3.86 | 4.76 | 8.62 |
| 312 | 97.56 | 3.13 | 6.45 | 9.59 |
| 333.5 | 97.55 | 2.86 | 6.96 | 9.82 |

Table 2 illustrates that the Rh-PhPy/Li/Y zeolite catalyst of the invention produces acetyl species at very high and commercially attractive rates for over 333 hours on stream at high methanol conversion

Example 3

Comparative

Example 3 is a comparative example illustrating preparation and use of a supported catalyst rhodium and 4-phenylpyridine (without lithium) on Rh-PhPy/Y zeolite (Rh-PhPy/Y) for vapor phase carbonylation of methanol to produce acetic acid (HOAc) and methyl acetate (MeOAc) in a fixed bed.

Rh-PhPy/Y zeolite was synthesized according to the same procedure of Example 2 above except the Li impregnating step onto the support was omitted.

The reactor was loaded with 6.3796 g (10 mL) of the Rh-PhPy/Y zeolite made above through the top of the reactor. The methanol carbonylation condition was the same as Example 1. The results are reported in Table III below.

TABLE III

| Hours | % MeOH conversion | moles MeOAc/L-hr | moles HOAc/L-hr | Net moles acetyl/L-hr |
|---|---|---|---|---|
| 2.00 | 98.91 | 0.60 | 4.56 | 5.16 |
| 5.17 | 99.48 | 1.42 | 10.38 | 11.79 |
| 27.50 | 97.09 | 2.82 | 7.01 | 9.83 |
| 56.50 | 91.63 | 3.57 | 3.89 | 7.46 |
| 72.00 | 88.65 | 3.33 | 2.79 | 6.12 |
| 74.00 | 86.34 | 3.65 | 2.84 | 6.49 |
| 76.00 | 86.37 | 3.47 | 2.66 | 6.13 |
| 78.00 | 87.29 | 3.00 | 2.18 | 5.19 |
| 80.50 | 83.80 | 3.77 | 2.64 | 6.41 |
| 96.00 | 84.82 | 3.50 | 2.31 | 5.80 |
| 99.00 | 81.45 | 3.67 | 2.16 | 5.83 |
| 101.00 | 80.93 | 3.28 | 1.75 | 5.03 |
| 103.00 | 81.16 | 3.11 | 1.71 | 4.82 |
| 120.50 | 80.15 | 3.29 | 1.72 | 5.00 |
| 122.50 | 80.84 | 3.24 | 1.58 | 4.82 |
| 124.50 | 81.00 | 3.21 | 1.60 | 4.81 |
| 148.75 | 79.53 | 3.14 | 1.35 | 4.49 |
| 173.00 | 80.53 | 3.17 | 1.28 | 4.45 |
| 192.25 | 78.75 | 3.25 | 1.26 | 4.52 |
| 214.75 | 74.36 | 2.70 | 0.89 | 3.59 |
| 228.00 | 71.91 | 2.58 | 1.00 | 3.58 |
| 245.75 | 72.63 | 2.56 | 1.09 | 3.65 |
| 264.00 | 72.49 | 2.52 | 1.06 | 3.58 |
| 291.00 | 81.80 | 3.12 | 1.75 | 4.87 |

Table 3 illustrates that the Rh-PhPy/Y zeolite catalyst deactivates significantly faster than Rh-PhPy/Li/Y zeolite of the invention.

Example 4

Example 4 illustrates preparing and use of supported rhodium, 4-phenylpyridine and lithium on a carbon support (Rh-PhPy/Li/Carbon) as catalyst for the vapor phase carbonylation of methanol to produce acetic acid (HOAc) and methyl acetate (MeOAc) in a fixed bed.

A Rh-PhPy/Li/Carbon solid supported catalyst was synthesized according to the following procedure. 0.5170 g of $RhCl_3.xH_2O$ (40% Rh) was dissolved in 20 g of deionized water and then using a rotary evaporator, impregnated to 20 g of activated spherical resin beads which were prepared as taught by United States Patent Application 2007/0191572A1. The mixture was heated using a water bath at a temperature of 60° C. and evacuated under 30 Torr of pressure until the resin beads became dry. The material was then refluxed with a solution with 2.5024 g 4-phenylpyridine in 25 ml of $CH_2Cl_2$ for 2 hours, and then dried under vacuum. The resulting Rh-PhPy/Carbon was then impregnated with Li from a solution prepared by dissolving 1.3318 g LiI in 20 ml deionized water. The resin was dried under vacuum to obtain the final catalyst suitable for the methanol carbonylation reaction.

The reactor was loaded with 8.7602 g (10 mL) of the Rh-PhPy/Li/Carbon made above through the top of the reactor. The methanol carbonylation condition was the same as Example 1. The results are reported in Table IV below.

TABLE IV

| Hours | % MeOH conversion | moles MeOAc/L-hr | moles HOAc/L-hr | Net moles acetyl/L-hr |
|---|---|---|---|---|
| 2.00 | 100.00 | 0.42 | 3.66 | 4.07 |
| 4.00 | 100.00 | 0.80 | 11.83 | 12.62 |
| 6.00 | 100.00 | 0.74 | 11.93 | 12.67 |
| 8.00 | 100.00 | 0.78 | 12.30 | 13.08 |
| 23.50 | 99.94 | 0.89 | 11.89 | 12.78 |
| 26.00 | 99.95 | 0.94 | 11.10 | 12.04 |
| 50.50 | 99.91 | 1.15 | 11.02 | 12.17 |
| 81.75 | 99.82 | 1.42 | 10.19 | 11.61 |
| 95.50 | 99.67 | 1.71 | 9.53 | 11.24 |
| 98.25 | 99.64 | 1.73 | 9.06 | 10.79 |
| 100.75 | 99.60 | 1.82 | 9.43 | 11.25 |
| 103.75 | 99.60 | 1.81 | 9.31 | 11.12 |
| 119.50 | 99.51 | 1.88 | 8.95 | 10.83 |
| 122.50 | 99.33 | 2.09 | 9.20 | 11.29 |
| 124.50 | 99.29 | 2.07 | 8.82 | 10.88 |
| 126.50 | 99.16 | 2.18 | 9.16 | 11.35 |
| 143.75 | 99.05 | 2.25 | 8.91 | 11.15 |
| 146.50 | 99.00 | 2.22 | 8.63 | 10.84 |
| 148.75 | 99.07 | 2.12 | 8.34 | 10.46 |
| 150.75 | 98.89 | 2.34 | 8.98 | 11.31 |
| 167.50 | 98.90 | 2.26 | 8.45 | 10.71 |
| 191.75 | 98.47 | 2.44 | 8.27 | 10.71 |
| 220.25 | 98.01 | 2.68 | 8.23 | 10.91 |
| 248.75 | 97.49 | 2.47 | 6.67 | 9.14 |
| 263.50 | 96.87 | 2.67 | 6.77 | 9.44 |
| 287.50 | 96.32 | 2.72 | 6.56 | 9.27 |
| 311.42 | 95.84 | 2.80 | 6.17 | 8.97 |
| 335.42 | 94.79 | 2.86 | 5.86 | 8.72 |
| 359.42 | 93.82 | 2.99 | 5.56 | 8.55 |

Table VI illustrates that the Rh-PhPy/Li/C catalyst of the invention produces acetyl species at very high and commercially attractive rates for over 359 hours on stream at high methanol conversion

Example 5

Example 5 illustrates the preparation and use of rhodium, 4-phenylpyridine and lithium on a silica support (Rh-PhPy/Li/silica) as catalyst for vapor phase carbonylation of methanol to produce acetic acid (HOAc) and methyl acetate (MeOAc) in a fixed bed.

Rh-PhPy/Li/silica solid supported catalyst was synthesized according to the following procedure: 0.5139 g of $RhCl_3.x H_2O$ (40% Rh) was dissolved in 100 g of deionized water and then using a rotary evaporator, impregnated into 20 g silica ES70W (available from INEOS Silicas 111 Ingalls Ave., Joliet, Ill. 60435). The mixture was heated using water bath at a temperature of 60° C. and evacuated under 30 Torr of pressure until the silica became dry. The material was then transferred to a quartz tube containing a quartz wool support plug. The quartz tube was placed into the Lindberg electric furnace and heated in an upward flow of nitrogen (100 SCCM) over a 2 hour period to 300° C. and held at 300° C. for 2 hours before cooling back to ambient temperature. The 15.03 g Rh/silica recovered from the quartz tube was then refluxed with a solution with 7.194 g 4-phenylpyridine in 25 ml of $CH_2Cl_2$ for 2 hours, and then dried under vacuum. Then the Rh-PhPy/silica was then impregnated with a solution prepared from dissolving 1.012 g LiI in 20 ml deionized water. The mixture again was dried and then transferred to a quartz tube containing a quartz wool support plug. The quartz tube was placed into the Lindberg electric furnace and heated in an upward flow of nitrogen (100 SCCM) over a 2 hour period to 300° C. and held at 300° C. for 2 hours before cooling back to ambient temperature to obtain the final catalyst suitable for the methanol carbonylation reaction.

The reactor was loaded with 5.4972 g (23 mL) of the Rh-PhPy/Li/silica made above through the top of the reactor. The methanol carbonylation condition was the same as Example 1. The results are reported in Table V below.

TABLE V

| Hours | % MeOH conversion | moles MeOAc/L-hr | moles HOAc/L-hr | Net moles acetyl/L-hr |
|---|---|---|---|---|
| 2.17 | 94.31 | 0.17 | 0.05 | 0.22 |
| 4.13 | 55.53 | 0.75 | 0.12 | 0.87 |
| 19.58 | 32.21 | 0.70 | 0.04 | 0.74 |
| 23.42 | 27.56 | 0.62 | 0.03 | 0.64 |
| 45.58 | 21.27 | 0.40 | 0.01 | 0.41 |

Table V illustrates that the Rh-PhPy/Li/silica catalyst produced acetyl species at very low rates for over 45 hours with low methanol conversion.

Example 6

Example 6 illustrates the preparation and use of rhodium, 4-phenylpyridine and lithium on modified silica (Rh-PhPy/Li/modified silica) on catalyst for vapor phase carbonylation of methanol to produce acetic acid (HOAc) and methyl acetate (MeOAc) in a fixed bed.

Rh-PhPy/Li/modified silica was synthesized according to the following procedure. 6.35 g of (3-chloropropyl) trimethoxysilane was dissolved in 100 mL of chloroform and then added to 20 g of silica ES70W from INEOS Silicas. The slurry was heated under reflux for 24 hours and then cooled to room temperature, at which point the solid was separated by filtration; washed with 50 mL of pentane, 100 mL of acetonitrile, and 100 mL of diethyl ether; and dried under vacuum, resulting in an intermediate Cl-Silica. The chloropropylated solid was then treated with 7.45 g 4-phenylpyridine/100 ml chloroform solution and heated under reflux for 24 hours. The slurry was cooled to room temperature, and the solid was separated by filtration, washed with 100 mL of toluene, and finally dried under ambient conditions. The solid was then impregnated with 0.518 g of RhCl$_3$ in 22 g of acetonitrile and dried in the vacuum oven at 100° C. overnight. The Rh-impregnated silica was then transferred to a quartz tube containing a quartz wool support plug. The quartz tube was placed into the Lindberg electric furnace and heated in an upward flow of nitrogen (100 SCCM) over a 2 hour period to 250° C. and held at 250° C. for 2 hours before cooling back to ambient temperature. The Rh-PhPy/modified silica was then impregnated with a solution prepared by dissolving 1.021 g LiI in 22 g acetonitrile and dried in the vacuum oven at 100° C. overnight. The Rh-PhPy/Li/modified silica again was then transferred to a quartz tube containing a quartz wool support plug. The quartz tube was placed into the Lindberg electric furnace and heated in an upward flow of nitrogen (100 SCCM) over a 2 hour period to 250° C. and held at 250° C. for 2 hours before cooling back to ambient temperature to obtain the final catalyst suitable for the methanol carbonylation reaction.

The reactor was loaded with 5.985 g (23 mL) of the Rh-PhPy/Li/modified silica made above through the top of the reactor. The methanol carbonylation condition was the same as Example 1. The results are reported in Table VI below.

TABLE VI

| Hours | % MeOH conversion | moles MeOAc/L-hr | moles HOAc/L-hr | Net moles acetyl/L-hr |
|---|---|---|---|---|
| 1.92 | 84.98 | 0.04 | 0.01 | 0.05 |
| 7.83 | 50.10 | 1.18 | 0.10 | 1.27 |
| 22.78 | 52.08 | 1.03 | 0.09 | 1.12 |
| 46.83 | 44.44 | 1.16 | 0.10 | 1.25 |
| 69.78 | 43.52 | 1.03 | 0.09 | 1.12 |
| 93.78 | 43.12 | 0.93 | 0.08 | 1.02 |
| 117.87 | 37.23 | 0.93 | 0.16 | 1.09 |
| 141.78 | 36.16 | 0.83 | 0.07 | 0.91 |
| 168.25 | 27.92 | 0.75 | 0.04 | 0.79 |
| 195.33 | 26.82 | 0.67 | 0.04 | 0.70 |
| 216.62 | 36.01 | 0.78 | 0.05 | 0.83 |
| 237.67 | 40.83 | 0.81 | 0.07 | 0.88 |
| 261.65 | 38.17 | 0.77 | 0.07 | 0.85 |
| 285.72 | 36.02 | 0.63 | 0.03 | 0.66 |

Table VI illustrates that the Rh-PhPy/Li/modified silica catalyst produces acetyl species at better rates than Rh-PhPy/Li/silica of Example 5.

Example 7

Example 7 illustrates the preparation and use of rhodium, 4-phenylpyridine and lithium supported on modified MCM-41 (Rh-PhPy/Li/modified MCM-41) as catalyst for the vapor phase carbonylation of methanol to acetic acid (HOAc) and methyl acetate (MeOAc) in a fixed bed.

Rh-PhPy/Li/modified MCM-41 was synthesized according to the following procedure. 7.2 g of (3-chloropropyl)trimethoxysilane was dissolved in 100 mL of chloroform and then added to 20 g of a mesoporous silica (MCM-41 available from Aldrich, 643645-25G). The slurry was heated under reflux at 62° C. for 24 hours and then cooled to room temperature. The solid was separated by filtration, washed with 50 mL of pentane, 100 mL of acetonitrile, and 100 mL of diethyl ether and dried under vacuum, resulting in the intermediate Cl-mesoporous silica. The chloropropylated solid was then treated with 7.32 g 4-phenylpyridine/100 ml chloroform and heated under reflux at 62° C. for 24 hours. The slurry was cooled to room temperature, and the solid was separated by filtration, washed with 100 mL of toluene, and finally dried under ambient conditions. The solid was impregnated with 0.598 g of RhCl$_3$ in 20 g of acetonitrile and dried in the vacuum oven at 100° C. overnight. The Rh-impregnated mesoporous silica was then transferred to a quartz tube containing a quartz wool support plug. The quartz tube was placed into the Lindberg electric furnace and heated in an upward flow of nitrogen (100 SCCM) over a 2 hour period to 250° C. and held at 250° C. for 2 hours before cooling back to ambient temperature. The Rh-PhPy/modified mesoporous silica was then impregnated with a solution prepared dissolving 1.70 g LiI in 22 g acetonitrile and dried in the vacuum oven at 100° C. overnight. The Rh-PhPy/Li/modified mesoporous silica again was then transferred to a quartz tube containing a quartz wool support plug. The quartz tube was placed into the Lindberg electric furnace and heated in an upward flow of nitrogen (100 SCCM) over a 2 hour period to 250° C. and held at 250° C. for 2 hours before cooling back to ambient temperature to obtain the final catalyst suitable for the methanol carbonylation reaction.

The reactor was loaded with 5.6942 g (23 mL) of the Rh-PhPy/Li/modified MCM-41 made above through the top of the reactor. The methanol carbonylation conditions were the same as set forth in Example 1 above. The results are reported in Table VII below.

TABLE VII

| Hours | % MeOH conversion | moles MeOAc/L-hr | moles HOAc/L-hr | Net moles acetyl/L-hr |
|---|---|---|---|---|
| 2.00 | 76.71 | 0.26 | 0.06 | 0.33 |
| 4.00 | 75.49 | 1.22 | 0.70 | 1.91 |
| 6.00 | 90.99 | 1.22 | 1.17 | 2.40 |
| 23.00 | 93.48 | 1.22 | 2.25 | 3.48 |
| 26.00 | 93.92 | 1.11 | 2.38 | 3.49 |
| 29.00 | 93.19 | 1.11 | 2.34 | 3.44 |
| 47.00 | 93.30 | 1.16 | 2.44 | 3.60 |
| 50.00 | 93.38 | 1.17 | 2.32 | 3.49 |
| 53.00 | 93.33 | 1.14 | 2.31 | 3.45 |
| 71.00 | 93.12 | 1.21 | 2.34 | 3.55 |
| 74.00 | 93.43 | 1.27 | 2.49 | 3.77 |
| 77.00 | 93.85 | 1.32 | 2.64 | 3.96 |
| 95.00 | 93.91 | 1.30 | 2.51 | 3.81 |
| 98.00 | 93.80 | 1.22 | 2.31 | 3.54 |
| 101.00 | 92.96 | 1.36 | 2.53 | 3.89 |
| 125.00 | 93.84 | 1.31 | 2.37 | 3.68 |
| 148.50 | 95.86 | 1.25 | 2.60 | 3.84 |
| 167.00 | 98.70 | 1.02 | 3.20 | 4.22 |
| 170.00 | 99.11 | 0.97 | 3.53 | 4.51 |
| 173.00 | 99.11 | 0.97 | 3.31 | 4.29 |
| 191.58 | 98.98 | 1.00 | 3.06 | 4.06 |
| 215.58 | 99.17 | 1.04 | 3.24 | 4.28 |
| 239.58 | 98.65 | 1.11 | 2.76 | 3.87 |
| 264.58 | 98.12 | 1.16 | 2.52 | 3.68 |
| 293.50 | 98.78 | 1.06 | 2.52 | 3.59 |

Table VII illustrates that the Rh-PhPy/Li/modified mesoporous silica catalyst produces acetyl species at much better rates than Rh-PhPy/Li/modified silica.

Example 8

Example 8 illustrates the preparation and use of iridium, ruthenium, rhodium, 4-phenylpyridine and zinc supported on Y zeolite (Ir/Ru/PhPy/Zn/Y zeolite) as catalyst for vapor phase carbonylation of methanol to produce acetic acid (HOAc) and methyl acetate (MeOAc) in a fixed bed.

Ir/Ru/PhPy/Zn/Y zeolite was synthesized according to the following procedure. 0.2078 g of RuCl$_3$ (45-55% Ru) was dissolved in 20 g of deionized H$_2$O and then impregnated into 20 g of 20-40 mesh crushed Y zeolite (having a silica/alumina ratio of 80) from Zeolyst using a rotary evaporator. The mixture was heated under water bath temperature 60° C. and evacuated under 30 Torr of pressure until it became dry. The material was then impregnated with 0.3535 g IrCl$_3$.xH$_2$O (54.36% Ir) dissolved in 20 g of deionized H$_2$O using the same procedure above. The material was then transferred to a quartz tube containing a quartz wool support plug. The quartz tube was placed into the Lindberg electric furnace and heated in an upward flow of nitrogen (100 SCCM) over a 2 hour period to 300° C. and held at 300° C. for 2 hours before cooling back to ambient temperature. The Ir—Ru/Y recovered from the quartz tube was then refluxed with a solution with 2.4966 g 4-phenylpyridine in 25 ml of CH$_2$Cl$_2$ for 2 hours, and then dried under vacuum. The Ir—Ru/PhPy/Y was then impregnated with a solution prepared from dissolving 2.1839 g (CH$_3$COO)$_2$Zn.2H$_2$O in 20 ml deionized water using a rotary evaporator and dried under vacuum for the methanol carbonylation reaction.

The reactor was loaded with 5.2216 g (10 mL) of the Ir/Ru/PhPy/Zn/Y zeolite made above through the top of the reactor. The methanol carbonylation conditions were the same as in Example 1. The results are reported in Table VIII below.

TABLE VIII

| Hours | % MeOH conversion | moles MeOAc/L-hr | moles HOAc/L-hr | Net moles acetyl/L-hr |
| --- | --- | --- | --- | --- |
| 2.00 | 71.56 | 0.44 | 0.08 | 0.52 |
| 4.00 | 49.89 | 1.38 | 0.08 | 1.45 |
| 6.00 | 83.54 | 2.42 | 5.29 | 7.71 |
| 23.25 | 71.88 | 2.97 | 1.50 | 4.47 |
| 26.00 | 66.52 | 2.64 | 0.35 | 2.99 |
| 28.25 | 67.13 | 2.51 | 0.16 | 2.67 |
| 30.25 | 72.35 | 2.15 | 0.13 | 2.28 |
| 47.00 | 62.46 | 3.00 | 0.17 | 3.17 |
| 49.00 | 60.38 | 2.97 | 0.24 | 3.21 |
| 51.25 | 59.87 | 2.88 | 0.17 | 3.05 |
| 54.25 | 59.70 | 3.01 | 0.18 | 3.20 |
| 71.25 | 58.03 | 2.86 | 0.15 | 3.01 |
| 74.50 | 58.06 | 2.71 | 0.26 | 2.98 |
| 99.50 | 50.19 | 2.61 | 0.17 | 2.78 |
| 128.00 | 51.15 | 1.92 | 0.10 | 2.01 |
| 142.75 | 42.23 | 1.82 | 0.07 | 1.88 |
| 146.00 | 41.11 | 1.70 | 0.06 | 1.76 |
| 150.00 | 41.69 | 1.66 | 0.05 | 1.71 |
| 166.75 | 38.41 | 1.56 | 0.05 | 1.61 |
| 190.83 | 34.03 | 1.37 | 0.09 | 1.46 |
| 214.83 | 29.82 | 1.19 | 0.04 | 1.23 |
| 238.83 | 28.17 | 1.07 | 0.02 | 1.09 |

Example 9

Example 9 illustrates the preparation and use of platinum, 4-phenylpyridine, lithium on Y zeolite (Pt-PhPy/Li/Y zeolite) as catalyst for the carbonylation of methanol to produce acetic acid (HOAc) and methyl acetate (MeOAc) in a fixed bed.

Pt-PhPy/Li/Y zeolite was synthesized according to the following procedure. 0.6706 g of PtCl$_4$ was dissolved in 20 g of deionized H$_2$O and then impregnated into 20 g of 20-40 mesh crushed Y zeolite from Zeolyst (having a silica/alumina ratio 80) using a rotovaporizer. The mixture was heated using a water bath temperature 60° C. and evacuated under 30 Torr pressure until it became dry. The material was then transferred to a quartz tube containing a quartz wool support plug. The quartz tube was placed into the Lindberg electric furnace and heated in an upward flow of nitrogen (100 SCCM) over a 2 hour period to 300° C. and held at 300° C. for 2 hours before cooling back to ambient temperature. The Pt/Y recovered from the quartz tube was then refluxed with a solution with 9.6152 g 4-phenylpyridine in 25 ml of CH$_2$Cl$_2$ for 2 hours, and then dried under vacuum. The Pt-PhPy/Y was then impregnated with a solution prepared by dissolving 1.3323 g LiI in 20 ml deionized water. The mixture again was dried under vacuum and then transferred to a quartz tube containing a quartz wool support plug. The quartz tube was placed into the Lindberg electric furnace and heated in an upward flow of nitrogen (100 SCCM) over a 2 hour period to 300° C. and held at 300° C. for 2 hours before cooling back to ambient temperature to obtain the final catalyst suitable for the methanol carbonylation reaction.

The reactor was loaded with 5.1006 g (10 mL) of the Pt-PhPy/Li/Y zeolite made above through the top of the reactor. The methanol carbonylation conditions were the same as Example 1. The results are reported in Table IX below.

TABLE IX

| Hours | % MeOH conversion | moles MeOAc/L-hr | moles HOAc/L-hr | Net moles acetyl/L-hr |
| --- | --- | --- | --- | --- |
| 2.00 | 74.64 | 0.04 | 0.01 | 0.05 |
| 4.00 | 40.01 | 0.08 | 0.01 | 0.08 |
| 6.00 | 34.83 | 0.07 | 0.01 | 0.08 |
| 21.66 | 26.79 | 0.07 | 0.00 | 0.08 |
| 25.16 | 17.81 | 0.09 | 0.01 | 0.09 |
| 27.16 | 17.86 | 0.09 | 0.01 | 0.09 |
| 29.16 | 22.37 | 0.08 | 0.01 | 0.09 |
| 45.08 | 20.31 | 0.08 | 0.01 | 0.08 |
| 47.08 | 27.76 | 0.07 | 0.01 | 0.08 |
| 49.08 | 7.71 | 0.09 | 0.01 | 0.10 |
| 51.08 | 16.49 | 0.08 | 0.01 | 0.08 |
| 53.08 | 29.89 | 0.06 | 0.00 | 0.07 |
| 69.08 | 17.19 | 0.08 | 0.00 | 0.08 |
| 72.08 | 17.88 | 0.08 | 0.01 | 0.09 |
| 75.08 | 20.27 | 0.07 | 0.00 | 0.08 |
| 77.08 | 15.65 | 0.09 | 0.01 | 0.09 |
| 93.16 | 18.78 | 0.07 | 0.00 | 0.07 |
| 120.74 | 18.17 | 0.07 | 0.00 | 0.07 |
| 149.40 | 15.56 | 0.07 | 0.00 | 0.08 |
| 166.48 | 15.99 | 0.06 | 0.00 | 0.07 |
| 172.48 | 17.14 | 0.06 | 0.00 | 0.07 |

Table IX illustrates that the Pt-PhPy/Li/Y zeolite catalyst produces acetyl species at much lower rates than Rh-PhPy/Li/Y zeolite.

Example 10

Rhodium, 2,2'-bipyridine and lithium on Y zeolite (Rh—BiPy/Li/Y zeolite) was synthesized according to the following procedure. 0.5216 g of RhCl$_3$.xH$_2$O (40% Rh) was dissolved in 20 g of deionized H$_2$O and then impregnated to 20 g of 20-40 mesh crushed Y zeolite from Zeolyst (having a silica/alumina ratio 80) using a rotary evaporator. The mixture was heated using a water bath temperature 60° C. and evacuated under 30 Torr of pressure until it became dry. The Rh/Y was then refluxed with a solution 2.5 g of 2,2'-bipyridine in 25 ml of CH$_2$Cl$_2$ for 17 hours and then dried under vacuum. One half of the Rh—BiPy/Y was then impregnated with a solution prepared from dissolving 0.667 g LiI in 10 ml deionized water and dried under vacuum.

The reactor was loaded with 7.4491 g (10 mL) of the Rh—BiPy/Li/Y zeolite made above through the top of the reactor. The loaded catalyst was heated in flow of helium at 200° C. overnight before methanol carbonylation reaction. The methanol carbonylation conditions were the same as Example 1. The results are reported in Table X below.

TABLE X

| Hours | % MeOH conversion | moles MeOAc/L-hr | moles HOAc/L-hr | Net moles acetyl/L-hr |
|---|---|---|---|---|
| 17.75 | 60.54 | 1.04 | 0.16 | 1.20 |
| 20.25 | 45.14 | 1.56 | 0.18 | 1.75 |
| 47.00 | 57.14 | 1.24 | 0.09 | 1.32 |
| 68.50 | 48.95 | 2.05 | 0.11 | 2.16 |
| 90.25 | 57.83 | 1.99 | 0.09 | 2.08 |
| 114.25 | 56.60 | 1.89 | 0.14 | 2.03 |
| 138.00 | 44.25 | 2.37 | 0.17 | 2.54 |
| 161.25 | 45.13 | 2.36 | 0.15 | 2.51 |
| 185.75 | 46.18 | 2.39 | 0.15 | 2.54 |
| 212.00 | 53.47 | 2.23 | 0.17 | 2.39 |
| 237.00 | 51.35 | 2.38 | 0.15 | 2.53 |
| 257.75 | 52.11 | 2.38 | 0.15 | 2.52 |
| 282.25 | 47.89 | 2.60 | 0.16 | 2.76 |
| 306.25 | 50.59 | 2.41 | 0.21 | 2.62 |

Example 11

Example 11 illustrates the use of rhodium, pyridine and lithium on Y zeolite (Rh-Py/Li//Y zeolite) in a liquid phase carbonylation of methanol to produce acetic acid (HOAc) and methyl acetate (MeOAc).

Rh-Py/Li/Y zeolite was synthesized according to the following procedure. Twenty grams (20 g) of Y zeolite from Strem Chemicals having silica/alumina ratio 5.6 were placed in an evaporating dish. 0.52 g of $RhCl_3.xH_2O$ (40% Rh) was dissolved in 20 g of deionized water. The Rh solution was added to the Y zeolite with stirring making sure the Y zeolite was uniformly wet. The impregnated Y zeolite was heated using a steam bath while stirring with a spatula until the material was dry. The Rh-impregnated Y zeolite was then transferred to a quartz tube containing a quartz wool support plug. The quartz tube was placed into the Lindberg electric furnace and heated in an upward flow of nitrogen (100 SCCM) over a 2 hour period to 300° C. and held at 300° C. for 2 hours before cooling back to ambient temperature. The resulting Rh/Y product recovered from the quartz tube was then refluxed with 30 ml pyridine for 2 hours, and dried using a nitrogen sweep by following evacuation. The Rh-Py/Y was then impregnated with a solution prepared by dissolving 1.324 g LiI in 20 ml water. The mixture again was dried over the steam bath. The Rh-Py/Li/Y was then transferred to a quartz tube containing a quartz wool support plug. The quartz tube was placed into the Lindberg electric furnace and heated in an upward flow of nitrogen (100 SCCM) over a 2 hour period to 300° C. and held at 300° C. for 2 hours before cooling back to ambient temperature to obtain the final catalyst suitable for the methanol carbonylation reaction.

Using a 300 mL Hastelloy® C-276 rocking autoclave, 2.43 g of Rh-Py/Li/Y zeolite, 28.8 g (0.9 mol) methanol, 14.2 g (0.1 mol) methyl iodide, 21.0 g (0.35 mol) acetic acid, and 1.8 g (0.1 mol) of water were added to the autoclave. The autoclave was sealed, flushed with nitrogen, and then pressurized to 350 psi (2.41 MPa) with CO. The mixture was heated to 180° C. Upon reaching temperature, the pressure adjusted to 800 psi (5.51 MPa) with CO. The temperature and pressure were maintained as the reaction was shaken for 1 hour. After 1 hour, the reaction was cooled, vented, and the product transferred to a sample bottle. Gas chromatograph analysis of the product indicated that the mixture contained 12.67 weight % methyl iodide, 32.19 weight % methyl acetate, 1.75 weight % methanol, 36.59 weight % acetic acid and 13.85 weight % water. This represented an acetyl production rate of 5.49 moles of acetyl/kg solution/hr. Inductively Coupled Plasma (ICP) analysis of the liquid product indicated that Rh concentration was 14.4 ppm. Accordingly only 4% of the Rh metal was leached from the support during liquid phase carbonylation. Thus, the catalyst achieved both favorable reaction rates and

Example 12

Comparative

Example 12 is a comparative example illustrating the use of unsupported rhodium chloride ($RhCl_3$) for the homogeneous liquid phase carbonylation of methanol to acetic acid (HOAc) and methyl acetate (MeOAc).

Liquid carbonylation conditions were the same as Example 11 except that 0.062 g (0.241 mmol) of $RhCl_3.xH_2O$ containing 40% Rh was used. Analysis of the product indicated that the mixture contained 15.66 weight % methyl iodide, 31.19 weight % methyl acetate, 1.07 weight % methanol, 43.30 weight % acetic acid and 12.08 weight % water. This represented an acetyl production rate of 7.08 moles of acetyl/kg solution/hr. ICP analysis of the liquid product indicated that Rh concentration was 278 ppm for the homogeneous catalyst.

Example 13

Comparative

Example 13 is a comparative example illustrating the use of rhodium alone (without lithium or any pyridine compound) on Y zeolite (Rh/Y zeolite) for liquid phase carbonylation of methanol to produce acetic acid (HOAc) and methyl acetate (MeOAc).

Rh/Y zeolite was synthesized according to the following procedure. Forty grams (40 g) of Y zeolite from Strem Chemicals with silica/alumina ratio 5.6 was placed in an evaporating dish. 1.04 g of $RhCl_3.xH_2O$ (40% Rh) was dissolved in 40 g of deionized water. The Rh solution was added to the Y zeolite with stirring making sure the Y zeolite was uniformly wet. The product was heated using a steam bath while stirring with a spatula until the material was dry. The Rh-impregnated Y zeolite was then transferred to a quartz tube containing a quartz wool support plug. The quartz tube was placed into the Lindberg electric furnace and heated in an upward flow of nitrogen (100 SCCM) over a 2 hour period to 300° C. and held at 300° C. for 2 hours before cooling back to ambient temperature.

Liquid carbonylation conditions were the same as Example 11 except that 2.43 g of this Rh/Y zeolite was used in place of catalyst from Example 11. Analysis of the product indicated that the mixture contained 13.79 weight % methyl iodide, 34.76 weight % methyl acetate, 1.89 weight % methanol, 37.13 weight % acetic acid and 14.30 weight % water. This represented an acetyl production rate of 5.83 moles of acetyl/kg solution/hr. ICP analysis of the liquid product indicated that Rh concentration was 337 ppm. Accordingly, 91% of the Rh metal was leached from the support during liquid phase carbonylation without the lithium and pyridine, a much higher leach rate than Example 11.

Example 14

Comparative

Example 14 is a comparative example illustrating the use of rhodium and lithium (without any pyridine compound) on Y zeolite (Rh/Li//Y zeolite) for the liquid phase carbonylation of methanol to produce acetic acid (HOAc) and methyl acetate (MeOAc).

Rh/Li/Y zeolite was synthesized according to the following procedure. Twenty grams (20 g) of Y zeolite from Strem Chemicals with silica/alumina ratio 5.6 was added to an evaporating dish. 0.52 g of $RhCl_3.xH_2O$ (40% Rh) was dissolved in 20 g of deionized water. The resulting Rh solution was added to the Y zeolite with stirring making sure the Y zeolite was uniformly wetted. The wetted Y zeolite was heated using a steam bath while stirring with a spatula until the material was dry. The Rh-impregnated Y zeolite was then transferred to a quartz tube containing a quartz wool support plug. The quartz tube was placed into the Lindberg electric furnace and heated in an upward flow of nitrogen (100 SCCM) over a 2 hour period to 300° C. and held at 300° C. for 2 hours before cooling back to ambient temperature. The dried Rh/Y was then impregnated with a solution prepared by dissolving 1.324 g LiI in 20 ml of deionized water. The mixture again was dried over the steam bath. The Rh/Li/Y again was then transferred to a quartz tube containing a quartz wool support plug. The quartz tube was placed into the Lindberg electric furnace and heated in an upward flow of nitrogen (100 SCCM) over a 2 hour period to 300° C. and held at 300° C. for 2 hours before cooling back to ambient temperature.

Liquid carbonylation conditions were the same as Example 11 except that 2.43 g of the Rh/Li/Y zeolite were used in place of catalyst from Example 11. Analysis of the liquid product indicated that the mixture contained 12.12 weight methyl iodide, 22.92 weight % methyl acetate, 0.44 weight % methanol, 55.40 weight % acetic acid and 8.64 weight % water. This represented an acetyl production rate of 9.08 moles of acetyl/kg solution/hr. ICP analysis of the product indicated that Rh concentration was 252 ppm. Accordingly, 72% of the Rh metal content was leached from the support during liquid phase carbonylation showing a much higher leach rate when the pyridine of Example 11 is not used.

Example 15

Comparative

Example 15 illustrates the use of Rh-Py/Y zeolite in a liquid phase carbonylation of methanol to produce acetic acid (HOAc) and methyl acetate (MeOAc).

Rh-Py/Y zeolite was synthesized according to the following procedure. Forty grams (40 g) of Y zeolite from Strem Chemicals having silica/alumina ratio 5.6 were placed in a flask. 75 grams of pyridine was added to the flask and stirred overnight under nitrogen to get 37 g of Pyridine Y. To the 37 grams of Pyridine Y, added 2.47 g of $RhCl_3.xH_2O$ (40% Rh) and 59 g methanol to the reaction. Heated to 65° C. and stirred for nine hours. After the solution cooled, solids were removed by filtration and washed with methanol, then dried in oven at 85° C. for 2 hours.

Using a 300 mL Hastelloy® C-276 rocking autoclave, 2.43 g of Rh-Py/Y zeolite, 28.8 g (0.9 mol) methanol, 14.2 g (0.1 mol) methyl iodide, 21.0 g (0.35 mol) acetic acid, and 1.8 g (0.1 mol) of water were added to the autoclave. The autoclave was sealed, flushed with nitrogen, and then pressurized to 350 psi (2.41 MPa) with CO. The mixture was heated to 180° C. Upon reaching temperature, the pressure adjusted to 800 psi (5.51 MPa) with CO. The temperature and pressure were maintained as the reaction was shaken for 1 hour. After 1 hour, the reaction was cooled, vented, and the product transferred to a sample bottle. Gas chromatograph analysis of the product indicated that the mixture contained 8.32 weight % methyl iodide, 38.82 weight % methyl acetate, 7.32 weight % methanol, 23.63 weight % acetic acid and 22.20 weight % water. This represented an acetyl production rate of 1.12 moles of acetyl/kg solution/hr. Inductively Coupled Plasma (ICP) analysis of the liquid product indicated that Rh concentration was 139.1 ppm. Approximately 40% of the Rh metal was leached from the support during liquid phase carbonylation. This example demonstrates that in the absence of Li, the Rh leaching is significantly higher and the rate or reaction is significantly lower than in Example 11.

Example 16

Comparative

Example 16 illustrates the use of Rh—Li/Carbon in a liquid phase carbonylation of methanol to produce acetic acid (HOAc) and methyl acetate (MeOAc).

Rh/Li/C was synthesized according to the following procedure. Thirty grams (30 g) of activated carbon was added to an evaporator dish. 3.63 g of $RhCl_3.xH_2O$ (40% Rh) was dissolved in 20 g of deionized water. The resulting Rh solution was added to the activated carbon with stirring making sure the activated carbon was uniformly wetted. The wetted carbon was heated using a steam bath while stirring with a spatula until the material was free flowing. The Rh-impregnated activated carbon was then transferred to a quartz tube containing a quartz wool support plug. The quartz tube was placed into the Lindberg electric furnace and heated in an upward flow of nitrogen (100 SCCM) over a 2 hour period to 300° C. and held at 300° C. for 2 hours before cooling back to ambient temperature. The Rh/Carbon was then impregnated with a solution prepared by dissolving 0.9287 LiI in 20 ml of deionized water. The mixture again was heated over the steam bath until material was free flowing. The Rh/Li/Carbon again was then transferred to a quartz tube containing a quartz wool support plug. The quartz tube was placed into the Lindberg electric furnace and heated in an upward flow of nitrogen (100 SCCM) over a 2 hour period to 300° C. and held at 300° C. for 2 hours before cooling back to ambient temperature.

Using a 300 mL Hastelloy® C-276 rocking autoclave, 3.41 g of Rh—Li/Carbon, 28.8 g (0.9 mol) methanol, 14.2 g (0.1 mol) methyl iodide, 21.0 g (0.35 mol) acetic acid, and 1.8 g (0.1 mol) of water were added to the autoclave. The autoclave was sealed, flushed with nitrogen, and then pressurized to 350 psi (2.41 MPa) with CO. The mixture was heated to 180° C. Upon reaching temperature, the pressure adjusted to 800 psi (5.51 MPa) with CO. The temperature and pressure were maintained as the reaction was shaken for 1 hour. After 1 hour, the reaction was cooled, vented, and the product transferred to a sample bottle. Gas chromatograph analysis of the product indicated that the mixture contained 10.39 weight % methyl iodide, 38.48 weight % methyl acetate, 6.75 weight % methanol, 24.42 weight % acetic acid and 21.52 weight % water. This represented an acetyl production rate of 1.01 moles of acetyl/kg solution/hr. Inductively Coupled Plasma (ICP) analysis of the liquid product indicated that Rh concentration was 22.2 ppm. Approximately 40% of the Rh metal was leached from the support during liquid phase carbonylation.

As can be seen by comparing Example with Comparative Examples 12-16 above, the combination of monomeric nitrogen compound and lithium in the solid supported catalyst of the present invention gives good acetyl production from methanol and unexpectedly can be utilized in both vapor phase and liquid phase carbonylation processes without a significant loss of activity or metal specie from the solid support.

Although the present invention has been shown and described in terms of the presently preferred embodiment(s), it is to be understood that various modifications and substitutions, rearrangements of parts, components and process steps can be made by those skilled in the art without departing from the novel spirit and scope of the invention.

We claim:

1. Carbonylation process for the production of esters, carboxylic acids or combinations of two or more of the foregoing comprising combining in a reaction zone at least one carbonylation feedstock compound selected from alkanols, dialkyl ethers, and combination of any two or more thereof with carbon monoxide in a carbonylation zone of a carbonylation reactor in the presence of a catalyst material, wherein the catalyst material comprises the contact product of:
    (a) a monomeric nitrogen-containing compound selected from pyridines and imidazoles;
    (b) a Group VIII metal; and
    (c) an alkali metal compound;
    wherein the catalyst material is on a solid support; and wherein said monomeric nitrogen-containing compound is selected from compounds having the structure of Formulas I and II:

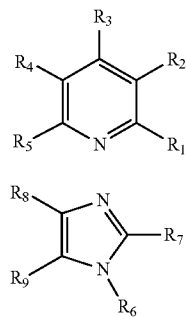

Formula I

Formula II wherein $R_1$, $R_2$, $R_3$, $R_4$, $R_5$, $R_6$, $R_7$, $R_8$ and $R_9$ are independently selected from hydrogen, substituted or unsubstituted, linear or branched-chained $C_1$-$C_{20}$ alkyl, substituted or unsubstituted cyclic $C_3$-$C_{20}$ alkyl, and substituted or unsubstituted $C_6$-$C_{20}$ aryl.

2. The carbonylation process of claim 1, wherein the monomeric nitrogen-containing compound is a structure of Formula I, and $R_1$, $R_2$, $R_4$, and $R_5$ are each independently selected from hydrogen and $C_1$-$C_3$ alkyl and $R_3$ is a phenyl group, said phenyl group being optionally substituted with a $C_1$-$C_{12}$ alkyl in a para-configuration around the phenyl ring with the other six-membered ring shown in Formula I.

3. The carbonylation process of claim 2, wherein $R_1$, $R_2$, $R_4$, and $R_5$ are each hydrogen.

4. The carbonylation process of claim 2, wherein $R_3$ is a phenyl group, said phenyl group being optionally substituted with a $C_1$-$C_3$ alkyl in a para-configuration around the phenyl ring with the other six-membered ring shown in Formula I.

5. The carbonylation process of claim 1 wherein said monomeric nitrogen-containing compound is 4-phenyl-pyridine.

6. The carbonylation process of claim 1, wherein the monomeric nitrogen-containing compound is a structure of Formula II, and $R_7$, $R_8$, and $R_9$ are each independently selected from hydrogen and $C_1$-$C_3$ alkyl and $R_6$ is a phenyl group, said phenyl group being optionally substituted with a $C_1$-$C_{12}$ alkyl in a para-configuration around the phenyl ring with the five-membered ring shown in Formula II.

7. The carbonylation process of claim 6, wherein $R_7$, $R_8$, and $R_9$ are each hydrogen.

8. The carbonylation process of claim 6, wherein $R_6$ is a phenyl group, said phenyl group being optionally substituted with a $C_1$-$C_3$ alkyl in a para-configuration around the phenyl ring with the five-membered ring shown in Formula II.

9. A carbonylation catalyst comprising the contact product of:
    (a) a monomeric nitrogen-containing compound selected from pyridines and imidazoles;
    (b) a Group VIII metal; and
    (c) an alkali metal compound;
    wherein the catalyst material is on a solid support; and wherein said monomeric nitrogen-containing compound is selected from compounds having the structure of Formulas I and II:

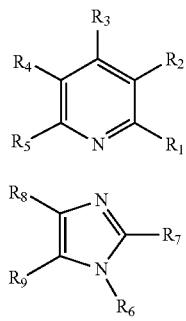

Formula I

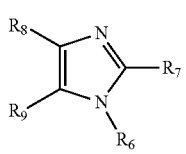

Formula II wherein $R_1$, $R_2$, $R_3$, $R_4$, $R_5$, $R_6$, $R_7$, $R_8$ and $R_9$ are independently selected from hydrogen, substituted or unsubstituted, linear or branched-chained $C_1$-$C_{20}$ alkyl, substituted or unsubstituted cyclic $C_3$-$C_{20}$ alkyl, and substituted or unsubstituted $C_6$-$C_{20}$ aryl.

10. The carbonylation catalyst of claim 9 wherein said monomeric nitrogen-containing compound is 4-phenyl-pyridine.

* * * * *